US008764685B2

(12) United States Patent
Casey (10) Patent No.: US 8,764,685 B2
(45) Date of Patent: Jul. 1, 2014

(54) BIOMEDICAL INTERFACE PRESSURE TRANSDUCER FOR MEDICAL TOURNIQUETS

(75) Inventor: Vincent Casey, Bruff (IE)

(73) Assignee: Abatis Medical Technologies Limited (IE)

( * ) Notice: Subject to any disclaimer, the term of this patent is extended or adjusted under 35 U.S.C. 154(b) by 0 days.

(21) Appl. No.: 13/491,415

(22) Filed: Jun. 7, 2012

(65) Prior Publication Data

US 2012/0330192 A1    Dec. 27, 2012

Related U.S. Application Data

(60) Provisional application No. 61/496,819, filed on Jun. 14, 2011.

(51) Int. Cl.
*A61B 5/021* (2006.01)
*A61B 5/022* (2006.01)

(52) U.S. Cl.
USPC ............ 600/587; 600/485; 600/486; 600/500

(58) Field of Classification Search
CPC ....... A61B 5/021; A61B 5/022; A61B 5/0215
USPC ................... 600/587, 485, 486, 500
See application file for complete search history.

(56) References Cited

U.S. PATENT DOCUMENTS

| 4,266,263 A * | 5/1981 | Haberl et al. ............... 361/283.2 |
|---|---|---|
| 4,526,043 A | 7/1985 | Boie et al. |
| 4,584,625 A | 4/1986 | Kellogg |
| 4,869,265 A | 9/1989 | McEwen |
| 5,195,375 A * | 3/1993 | Tenerz et al. .................. 73/705 |
| 5,693,886 A * | 12/1997 | Seimiya et al. ................. 73/718 |
| 5,722,414 A * | 3/1998 | Archibald et al. ............ 600/485 |
| 6,636,760 B1 | 10/2003 | Casey |
| 6,759,769 B2 * | 7/2004 | Kirjavainen .................. 307/400 |
| 2003/0097073 A1 * | 5/2003 | Bullister et al. .............. 600/486 |
| 2006/0211914 A1 * | 9/2006 | Hassler et al. .................. 600/37 |
| 2007/0167879 A1 * | 7/2007 | Cochran ....................... 600/595 |

(Continued)

FOREIGN PATENT DOCUMENTS

WO    2006030405    3/2006

OTHER PUBLICATIONS

Partsch, H., et al. "Meausrement of Lower Leg Compression in Vivo: Recommendations for the Performance of Measurements of Interface Pressure and Stiffness," Dermatol Surg, vol. 32 (No. 2), 224-232, (2006).*

(Continued)

*Primary Examiner* — Sean Dougherty
*Assistant Examiner* — Daniel Cerioni
(74) *Attorney, Agent, or Firm* — Hancock Hughey LLP (57) ABSTRACT

A biomedical interface pressure transducer which is useful for interposing between a limb or tissue and an occlusive band, tourniquet cuff or other biomedical apparatus in order to estimate the pressure and pressure gradient applied to a selected area of the limb or tissue is disclosed. The pressure transducer comprises a modified MEMS pressure sensor and a conformable semisolid body enclosed in a shear relief membrane which translates the pressure applied by the occlusive band to the modified MEMS pressure sensor mounted on a flexible substrate with patterned electrical interconnect tracks allowing the connection of the pressure sensor to digital communication and control circuitry.

16 Claims, 5 Drawing Sheets

(56) References Cited

U.S. PATENT DOCUMENTS

2009/0085444 A1* 4/2009 Alvarez Icaza Rivera et al. .............. 310/365
2009/0270740 A1* 10/2009 Keilman et al. ............... 600/486
2011/0066046 A1* 3/2011 Young et al. ................. 600/486

OTHER PUBLICATIONS

Wise, K., "Integrated sensors, MEMS< and microsystems: Reflections on a fantastic voyage," Sensors and Actuators A: Physical, vol. 136, 39-60, (2007).*

Measurement Specialties, Inc., Pressure Sensor—MS54xx, retrieved at http://web.archive.org/web/20101126054100/http://meas-spec.com/product/t_product.aspx?id=5021, Nov. 26, 2010.*

Doyle and Taillac, "Tourniquets: A Review of Current Use with Proposals for Expanded Prehospital Use", Prehospital Emergency Care, V12, 2008, 241-54.

Nordin et al. entitled "Surgical Tourniquets in Orthopaedics" published in The Journal of Bone & Joint Surgery (2009; 91: 2958-2967).

V. Casey, S. Griffin and S. B. G. O'Brien, "An investigation of the hammocking effect associated with interface pressure measurements using pneumatic tourniquet cuffs", Medical Engineering & Physics, V23, 2001, pp. 513-519.

S. B. G. O'Brien and V. Casey, "Asymptotic and numerical solutions for a hammocking model", Quarterly Journal of Mechanics and Applied Mathematics, V55, 2002, pp. 409-420.

Intersema Application Note AN401, entitled Analog Sensor Interfacing; Jan 31, 2003; 5 pages.

* cited by examiner

BIOMEDICAL INTERFACE PRESSURE TRANSDUCER FOR MEDICAL TOURNIQUETS

FIELD OF THE INVENTION

This invention pertains to transducers for estimating the pressure and pressure gradients applied to body-tissue by an object such as pneumatic tourniquet used in surgical procedures and in tactical and civilian emergency medical services (EMS).

BACKGROUND OF THE INVENTION

The pressure, P, developed beneath a pneumatic tourniquet cuff is largely governed by the gas or fluid pressure $\pi$ in the tourniquet, which is assumed to act normally to the local support surface. In many practical instances of pneumatic tourniquet use, P is assumed to be equal to $\pi$. However, there are situations where this assumption may not be valid. In such cases hazard conditions can arise due to discrepancies between the indicated cuff pressure, $\pi$, and the actual applied pressure P. For instance, the outer walls of some pneumatic cuffs have integrated stiffener layers designed to stabilize and restrict radial expansion of the cuff when fitted to a supporting limb. The overall cuff geometry may be linear with oval cross section. When cuffs with such geometry are wrapped onto a limb and inflated, the inner wall membranes will necessarily fold and crease to accommodate the reduced circumferential scale. Such folding and creasing complicates the local stress field which may have significant orientation and magnitude variation producing wrinkling and pinching of the support tissue. Contoured cuffs and cuffs matched to limb size have been developed that greatly reduce this and other risks that can arise with simpler cuff geometries. Nevertheless, the inner wall membranes of such cuffs may support residual shearing and torsional forces and these may contribute additional components to the pressure P actually applied to the supporting tissue which is not reflected in the tourniquet measured pressure $\pi$.

Similarly, an over-tight un-inflated cuff may result in tissue applied pressures, P, sufficient to occlude venous return while indicating zero inflation pressure, $\pi$. Accidental blockages of the fluid lines used with pneumatic tourniquet cuffs can give rise to indicated cuff pressures, $\pi$, which can be higher or lower, depending upon the circumstances of the blockage, than the pressure in the cuff and consequently be unrepresentative of the actual tourniquet applied pressure P.

The use of soft, wrinkle-free padding (eg, cotton cast padding, stockinette, bandage) between the patient's limb and the tourniquet cuff is recommended by some pneumatic tourniquet cuff manufacturers in order to reduce cuff induced shear forces which can constitute a significant injury risk to soft tissue. However, such interventions may produce an offset or residual non-pneumatic pressure of unknown value resulting in a discrepancy between tourniquet pressure, $\pi$, and actual applied pressure, P. Again, such non-pneumatic pressures may be sufficiently high to restrict venous return from the supporting limb and impede the flow of arterial blood into the limb.

In non-pneumatic tourniquets commonly used in tactical and civilian emergency medical services (EMS) to restrict blood loss, the applied pressure is governed by the tension, T, in the tourniquet membrane or strap and the curvature, $\kappa$, of the membrane according to the law of Laplace, $P=T\kappa$. In the case of membranes applied to cylindrical bodies, i.e. a membrane tourniquet on a limb, the form $P=NT/r$ is frequently used by clinicians to estimate the applied pressure, where N is the number of complete wraps, r is the radius of curvature of the limb and the wrapping tension T is assumed to be constant. However, real limbs do not have regular geometric shapes and so the pressure will vary locally with curvature. In addition, the actual membrane tension may not be measured or known. Pressures calculated using the law of Laplace cannot be expected to accurately reflect the actual sub-tourniquet pressure at a given location on a limb or support tissue nor can such calculations provide a dynamic indication of the actual pressure applied by the tourniquet as limb position and orientation changes. A major criticism of such tourniquets used to restrict arterial blood flow, is that, if not properly applied, tourniquets can actually increase bleeding by occluding venous return while not completely arresting arterial flow {Doyle and Taillac, "Tourniquets: A Review of Current Use with Proposals for Expanded Prehospital Use", Prehospital Emergency Care, V12, 2008, 241-54}.

The risk of tourniquet-related nerve injury continues to be a serious concern. Large sub-tourniquet pressure gradients have been identified as a significant contributory factor in a recent paper by Nordin et al. entitled "Surgical Tourniquets in Orthopaedics" published in The Journal of Bone & Joint Surgery (2009; 91: 2958-2967). The use of wider cuffs, where practicable, can reduce the size of such gradients.

In these and other biomedical applications it is desirable to have a transducer which may be located at the biomedical interface between the tourniquet and the limb which establishes the actual pressure applied by the tourniquet to the underlying support tissue, in a continuous way, throughout a medical procedure but also while the tourniquet is being applied to, and removed from the limb or tissue. The availability of such a transducer would greatly enhance patient safety and reduce the level of operator skill required in the routine use of tourniquets. Likewise, the availability of a reliable biomedical interface pressure gradient transducer would allow the development of enhanced tourniquet safety features designed to reduce the risk of nerve and deep tissue injury.

While there are biomedical pressure sensor devices available which may be placed between the tourniquet and the supporting limb or tissue, such sensors are necessarily intrusive and significant errors can arise due to the so called 'hammocking-effect' whereby a membrane such as bandage, cuff liner or indeed skin, stretches and curves in order to adjust to the shape of the sensor. In the case of a tourniquet on a limb, the tourniquet membrane lifts away from the supporting tissue in the vicinity of the sensor forming a profile somewhat like that of a hammock. The active sensor area is a critical parameter in the calibration of pressure sensors. It is normal to assume a constant active area based upon the geometric area of the sensor. However, the 'hammocking-effect' changes the effective area of the sensor which in turn varies with applied pressure/tension in a complex manner. Consequently, it is difficult to calibrate such sensors reliably for the wide range of tissue properties, curvatures and tourniquet membrane properties encountered in actual biomedical application environments.

Pneumatic tourniquets present further challenges in relation to the direct measurement of interface pressures generated when tourniquets are applied to limbs and tissue. As already described, the inner membranes of such tourniquets may buckle and fold and thereby support complex forces. Instead, normal and shear forces will co-exist and act on any sensor deployed at the interface. Pressure sensors are optimized for hydrostatic pressure measurement and so have optimum performance when the target pressure is relayed via fluid such as gas or liquid to the primary transduction element which is normally a cantilever or diaphragm. Without such a fluid, shear forces can result in large spurious pressure indications. Consequently, pressure measurement systems used in biomedical pressure measurement tend to use fluid lines to relay the pressure from the target measurement site to a sensor which is remote from the target environment (eg patent U.S. Pat. No. 4,584,625 disclosed by Kellogg describes a capacitive tactile sensor having gas-filled compression cells). However, the use of fluid lines has serious disadvantages for biomedical pressure applications. Fluid lines present a serious risk of error through partial or total obstruction due to folding and kinking of the lines. There is also a risk of fluid leak and contamination. Singly or combined these risks can present a significant safety risk to patients.

In WO2006030405, a low profile, flexible and planar biomedical pressure transducer is disclosed which greatly reduces the influence of the hammocking-effect on indicated pressures. This device is optimized for use as an interface pressure sensor for relatively low pressure applications such as bandaging and compression therapy. Such devices are not suitable for tourniquet applications where applied pressures may be as high as 500 mmHG and the interface region is subject to complex force fields.

U.S. Pat. No. 4,869,265 describes a biomedical pressure transducer having a pressurizable chamber containing integral membrane switch type electrical contacts interposed between the tissue and an apparatus such as a tourniquet cuff. The normally closed contacts are opened when the pressure within the chamber is equal to the pressure applied by the cuff. This approach does not appear to provide a continuous dynamic estimate of the pressure applied and suffers from signal damping introduced by the fluid line. In addition, this device appears to be complex.

In a planar transducer disclosed in U.S. Pat. No. 6,636,760 a structured elastomer element is used in a fiber optic based semi-rigid sensor suitable for use in the measurement of pressures under surgical tourniquet cuffs. Component alignment is critically important for such devices. This complicates the fabrication process and results in devices which are substantially rigid and intrusive requiring frequent calibration checking U.S. Pat. No. 6,526,043 (Boie et al) describes a tactile transducer having a planar deformable layer and multiple conductive elements on each side. The arrangement is complex requiring sophisticated processing in order to infer precise pressure values.

Of the various electrical device properties which may be exploited in pressure transducers, electrical resistance is the easiest one to measure precisely over a wide range at moderate cost. Microelectromechanical system (MEMS) pressure sensor devices are widely available for general purpose, low cost, pressure measurement. These devices are typically piezoresistive, transforming a mechanical stress into a resistance signal which may be further transformed, through suitable electronic processing, into a pressure signal. Accordingly, this invention is directed towards providing an improved transducer for measuring biomedical interface pressures and pressure gradients at any interface between a human limb or tissue and a pneumatic or non-pneumatic tourniquet, using low cost, pre-calibrated, dynamic MEMS pressure sensors as the active pressure sensing element.

The applicant is aware of the following published references which are more or less relevant to the subject matter of the applicant's invention: V. Casey, S. Griffin and S. B. G. O'Brien, "An investigation of the hammocking effect associated with interface pressure measurements using pneumatic tourniquet cuffs", Medical Engineering & Physics, V23, 2001, pp. 513-519; S. B. G. O'Brien and V. Casey, "Asymptotic and numerical solutions for a hammocking model", Quarterly Journal of Mechanics and Applied Mathematics, V55, 2002, pp. 409-420; Intersema Application Note AN401, entitled Analog Sensor Interfacing.

SUMMARY OF THE INVENTION

This invention is directed towards providing an improved transducer for measuring biomedical interface pressures and pressure gradients at any interface between a human limb or tissue and a pneumatic or non-pneumatic tourniquet, using low cost, pre-calibrated, dynamic MEMS pressure sensors as the active pressure sensing element.

BRIEF DESCRIPTION OF THE DRAWINGS

The invention will be more clearly understood from the following description of some embodiments thereof, given by way of example only with reference to the accompanying drawings in which.

DETAILED DESCRIPTION OF THE EMBODIMENTS

Figure 1:
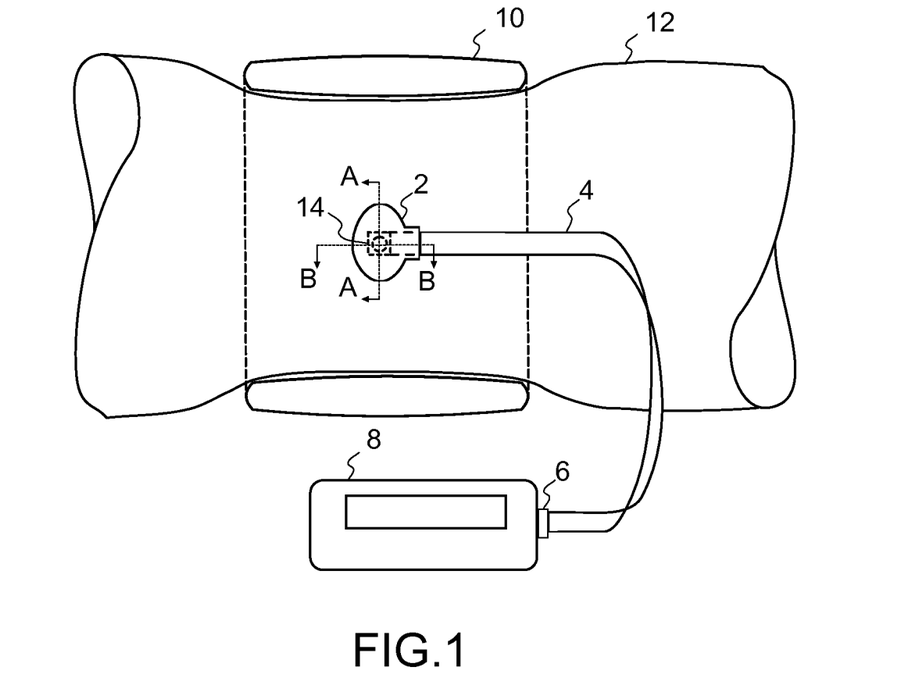
FIG. 1 is a schematic diagram depicting a biomedical interface pressure transducer disposed between a tourniquet and a human limb as well as electronic control means.

A biomedical interface pressure transducer apparatus is shown in FIG. 1 and consists of: biomedical interface pressure transducer 2, flexible interconnector assembly 4, connector 6 and control means 8. The biomedical interface pressure transducer 2 is disposed between a pneumatic tourniquet 10 and a limb 12 and incorporates a modified MEMS pressure sensor 14. The transducer may be positioned at a desired location under the tourniquet using medical adhesive tape or adhesive pads.

In overview, the pneumatic tourniquet 10 applies pressure to the enclosed limb 12. The biomedical interface pressure transducer 2 is located at the interface between the pneumatic tourniquet 10 and the limb surface. Control means 8 includes a user interface that permits a user to control the operation of the biomedical interface pressure transducer 2. The control means 8 displays relevant information regarding the operation of the biomedical interface pressure transducer 2 to the user. The user interface of control means 8 permits a user to: enter calibration constants and temperature compensation coefficients; set reference levels such as zero pressure; set alarm limits for interface pressures produced by pneumatic tourniquet 10; display estimates of the interface pressure produced by pneumatic tourniquet 10 at the limb surface; store estimates of the interface pressure logged at user defined time intervals; display a plot of the interface pressure time profile. Control means 8 includes a standard USB communication interface which permits interfacing with other monitoring and control instruments including computers.

Figure 2:
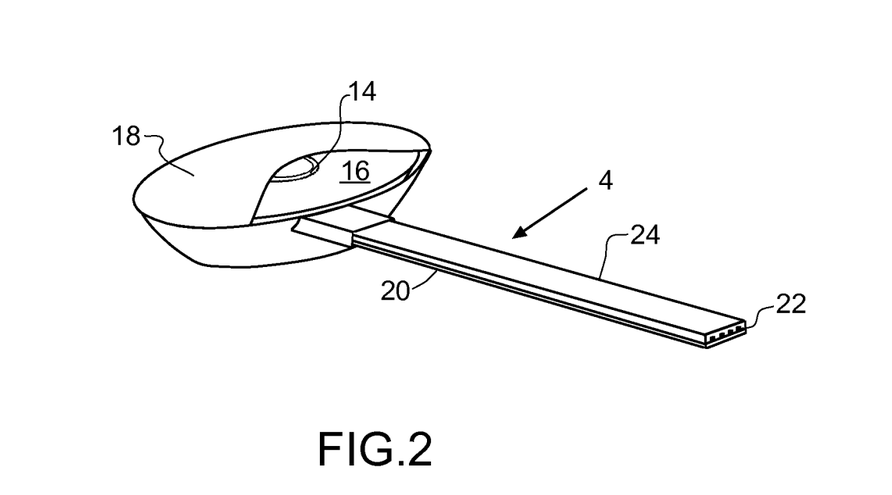
FIG. 2 is a pictorial view, partially broken away for illustration, showing a preferred embodiment of a biomedical interface pressure transducer constructed in accordance with the present invention.

A pictorial representation of one embodiment of the biomedical interface pressure transducer 2 is presented in FIG. 2. The transducer comprises a conformable semisolid body 16, which is encapsulated in a loosely fitted shear relief membrane 18. The inner surface of the shear relief membrane 18 which is in contact with the conformable semisolid body 16 and MEMS pressure sensor 14, partially visible in FIG. 2, is coated with a thin film of lubricant. Electrical connection to the modified MEMS pressure sensor 14 is made via a flexible substrate 20 with integrated electrical patterned conductor 22 tracks which together with electrical insulation 24, comprises the flexible interconnector assembly 4.

The conformable semisolid body 16 has the general shape of a planar ellipsoid (FIGS. 1 and 2) of thickness less than 4 mm. In use, the conformable semisolid body 16 may be orientated with its major axis aligned with the limb circumference of major curvature and its minor axis orientated along the limb axis as shown in FIG. 1. When the pneumatic tourniquet 10 applies pressure to the limb, the conformable semisolid body 16 conforms to the shape of the supporting limb 12 as illustrated by means of cross-section shown in FIG. 3, thereby reducing the intrusiveness of the transducer. Pressure at the surface of the limb 12 is transmitted via the shear relief membrane 18 to the modified MEMS pressure sensor 14. The shear relief membrane 18 has limited freedom to move laterally with respect to the conformable semisolid body 16, and the modified MEMS pressure sensor 14 within the constraints imposed by the closeness of fit of the membrane to the conformable semisolid body 16. Shear forces which may exist between the tourniquet 10 and the conformable semisolid body 16 with integral modified MEMS pressure sensor 14, and the limb 12 surface, are substantially reduced by the combined effects of the shear relief membrane 18 and the lubricant coating.

Figure 3:
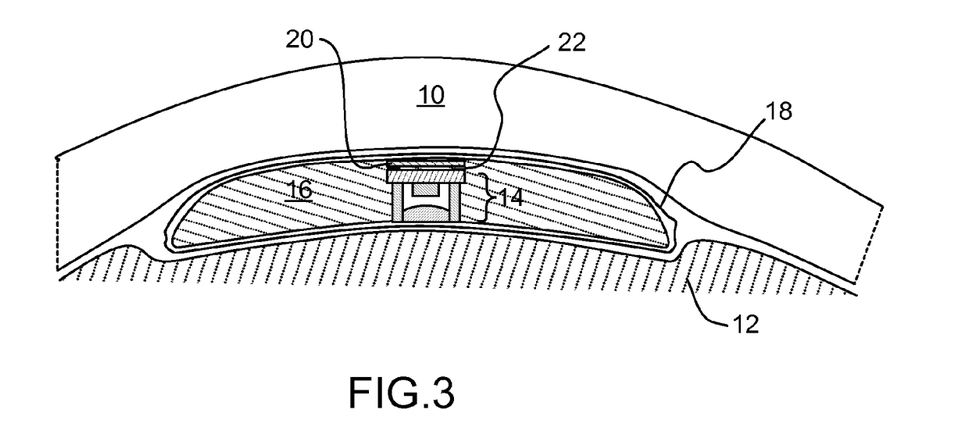
FIG. 3 is a cross-sectional view in the direction of the arrows A-A of FIG. 1 showing details of the biomedical interface pressure transducer construction of the invention.
Figure 4:
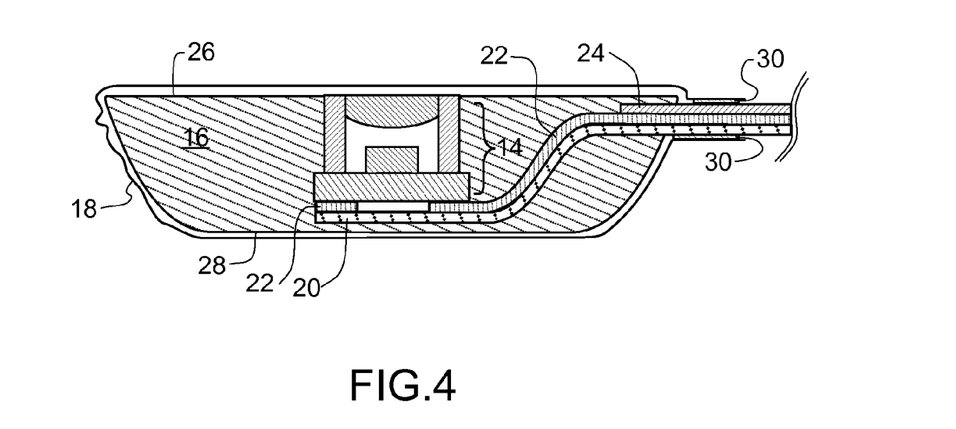
FIG. 4 is an inverted cross-sectional view in the direction of the arrows B-B of FIG. 1 showing details of the biomedical interface pressure transducer construction of the invention.
Figure 5:
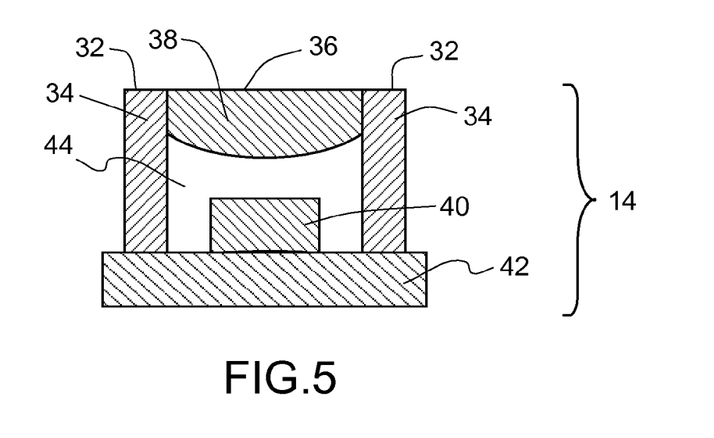
FIG. 5 is an exploded cross section view of the modified MEMS pressure sensor of FIGS. 3 and 4.

An inverted cross-section of the biomedical interface pressure transducer 2 of this invention illustrating details of its construction is shown in FIG. 4. FIG. 5 shows an exploded view of the modified MEMS pressure sensor 14 of this invention. The sides of the conformable semisolid body 16 are curved between the top planar face 26 that is normally orientated towards the tissue and the bottom planar face 28 normally orientated towards the tourniquet in such a way as to present a gently contoured transition between the faces (FIGS. 3 and 4). A modified MEMS pressure sensor 14 is surface mounted onto a flexible substrate 20 such as Kapton® (DuPont) polyimide film with patterned conductor 22 tracks used commonly in the flexible circuitry industry. The conformable semisolid body 16 may be formed from polydimethyl siloxane (PDMS) (Dow Corning, Sylgard 184), or other such elastomer. The thickness extent of the conformable semisolid body 16 is such as to span the vertical extent of the modified MEMS pressure sensor 14 plus flexible substrate 20. In order to minimize hammocking related measurement artefacts, the top planar face 26 of the conformable semisolid body 16 must be substantially coplanar with the top surface 32 of the MEMS pressure sensor port 34 and the top surface 36 of the media isolation material 38 as illustrated in FIGS. 4 and 5. The bottom planar face 28 of the conformable semisolid body 16 is substantially parallel to the top planar face 26 of the conformable semisolid body 16 and may encapsulate the flexible substrate 20 where it supports the modified MEMS pressure sensor 14. However, as such encapsulation adds to the overall thickness of the transducer, it is preferably reduced to zero or small fractions of a millimeter where it covers the flexible substrate 20. The side walls of the conformable semisolid body 16 are formed in the shape of an arc or other such tapered profile in order to allow continuous intimate contact between the biomedical interface pressure transducer 2 and the pneumatic tourniquet 10 and limb 12 respectively. An insulating layer 24 covers the patterned conductor 22 tracks and may extend some distance into the conformable semisolid body 16 as illustrated in FIG. 4. The shear relief membrane 18 is a non-stretch, low friction, smooth (non-woven) film material such as nylon or other medically approved polymer. A lubricant such as Vaseline (paraffin wax), or ion free medical gel is coated onto all areas of the inner surface of the shear relief membrane other than the region which is to be adhesively joined to the flexible interconnector assembly 4 using adhesive 30, or radio frequency- or ultrasonic-welding.

The sensor chip 40 is a micromachined piezoresistive pressure sensor mounted onto a solid substrate 42. An example of such a sensor is manufactured by Measurement Specialties Inc, and is described in detail in the datasheet covering the MS54 series of devices by this manufacturer. The MEMS sensor volume defined by the pressure sensor port 34 is partially filled with MEMS protection material 44 such as a soft ion free silicone gel (Dow Corning, Sylgard 527) with viscosity less than 1000 cps and low hardness which has been degassed by enclosing in a vacuum chamber pumped by a roughing pump for 10 minutes. The MEMS protection material 44 covers the MEMS sensor chip 40 and associated bond wires while leaving room for a thin media isolation material 38. The media isolation material 38 fills the remaining pressure sensor port 34 volume providing a top surface 36 which is substantially coplanar with the top surface 32 of the MEMS pressure sensor port 34. The function of this material is to provide a robust, non-stick interface which may contact continuum materials such as membranes and tissue and at the same time faithfully translate the pressure applied by the continuum material via the shear relief membrane 18 to the MEMS protection material 44 and MEMS chip 40. The media isolation material 38 may be selected from a range of materials with different Durometer-Shore A hardness index such as RTV Silicone (Dow Corning), polydimethyl siloxane (PDMS) (Dow Corning, Sylgard 184), Silicone Rubber (T20 and T28, Alec Tiranti Limited, Berkshire, UK) and Rubison premixed white silicone. The media isolation material 38 thickness may optimally range from 0.5 mm to 1.0 mm at the point of maximum thickness. Materials with higher Durometer-Shore A index need to be thinner, in general, than softer (low Durometer-Shore A index) materials in order to avoid media isolation material 38 induced sensor response time damping, hysteresis, and sensitivity reduction. The media isolation material 38 may be degassed at 710-740 mmHg vacuum for 20 minutes before use.

Figure 6:
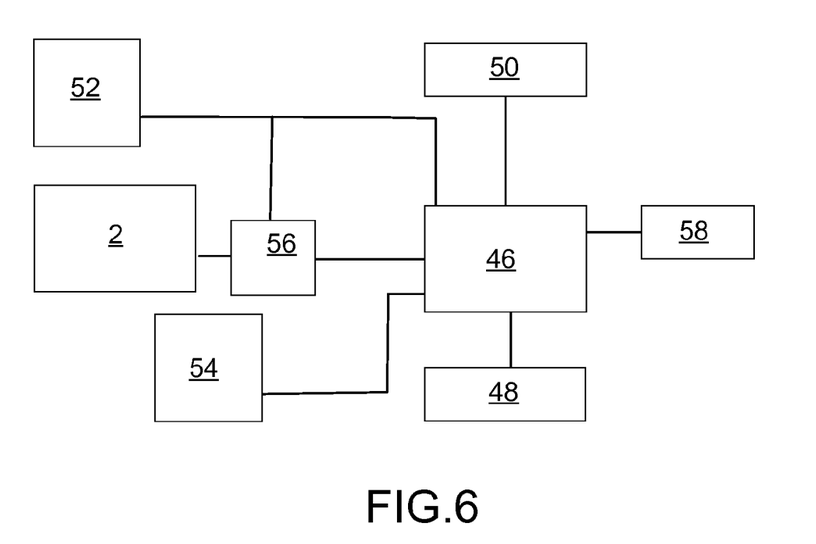
FIG. 6 is a block diagram showing a schematic representation of the major components of the control means.

A zero insertion force (ZIF) connector 6 such as those manufactured by Berg Ltd. may be used to provide a make-break connection between the control means 8 and the flexible interconnector assembly 4. The control means 8 comprises a microcontroller 46 with integral analogue to digital converter, memory, control and display driver circuits, FIG. 6. The microcontroller 46 is connected to a keypad 48 and a digital display 50. Power for the microcontroller is provided by the power supply 52 and a clock signal is provided by the crystal oscillator 54. The microcontroller 46 provides power to the biomedical interface pressure transducer 2 via the signal processing circuit 56 and samples the analogue voltage signal from the biomedical interface pressure transducer 2 after processing in the signal processing circuit 56. Signal processing circuit 56 provides a degree of temperature compensation of span and offset voltage and is designed along principles outlined in Intersema Application Note, AN401. The system may be conveniently calibrated by applying two known pressures, typically 0 and 150 mmHg (gauge pressure) to the biomedical interface pressure transducer 2 equilibrated at anticipated on-body/use temperature (37° C.) and by microcontroller software adjustment of the digital signal using calibration coefficients in order to convert to desired engineering pressure units for display via the digital display 50. The calibration coefficients may be entered manually from a table of known values using the keypad 48 or determined experimentally by following a calibration sequence of instructions provided by microcontroller resident software. The calibration coefficients may be conveniently stored in the microcontroller 46 memory. The overall pressure measurement sequence may be completed within 1 ms thereby providing a dynamic signal measurement rate of 1 kHz. Interface pressure readings may be stored within the microcontroller memory for later recall and display or alternatively may be streamed to a computer or data logger via the USB interface 58 or other standard instrumentation interface, for further analysis, manipulation and display. Similarly, the controller may be programmed using a computer attached to it via the USB interface 58 or other standard interface.

Figure 7:
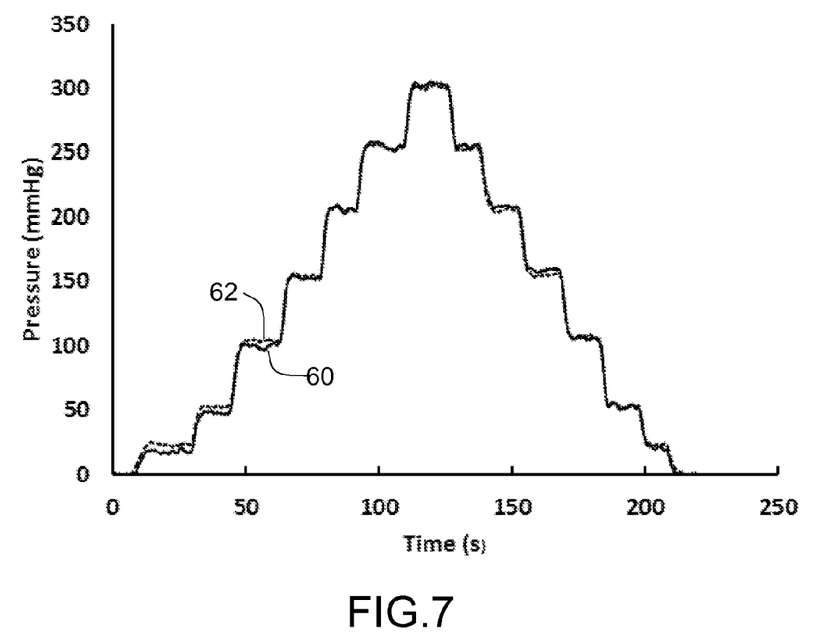
FIG. 7 shows two contemporaneous dynamic pressure signal curves obtained for a surgical pneumatic tourniquet supported on a patient's limb with a biomedical interface pressure transducer of this invention positioned between the tourniquet and the tissue as illustrated in FIG. 1. One curve is derived from the biomedical interface pressure transducer of this invention and the other is obtained from a pressure sensor coupled to the inflation gas-line of the pneumatic tourniquet.
Figure 8:
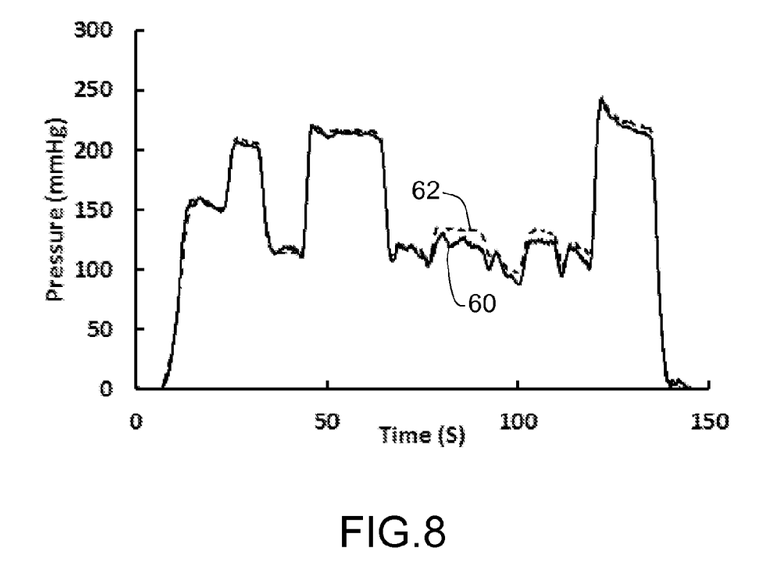
FIG. 8 is an output display illustrating the course of the biomedical interface pressure transducer indicated interface pressure as a pneumatic tourniquet is applied to a human limb and inflated to 150 mmHg approximately. Subsequent pressure variations are due to limb twisting and muscle flexing. The tourniquet gas-line inflation pressure is also shown for reference.

FIGS. 7 and 8 contain plots of data obtained using the biomedical interface pressure transducer apparatus of this invention. The interface pressure curve 60 represents the continuous data stream from the biomedical interface transducer as tourniquet cuff inflation pressure 62 varies in step changes, FIG. 7, and due to muscle flexing and limb twisting at a datum pressure of 150 mmHg, FIG. 8. The data demonstrates the responsiveness of the transducer to changes in cuff inflation pressure and shows that the transducer gives a faithful dynamic representation of the interface pressure for a properly fitted cuff on a limb. Discrepancies between biomedical interface pressure transducer data and cuff inflation data are indicative of improperly fitted cuffs or non-pneumatic pressure sources and shear artefacts.

Figure 9:
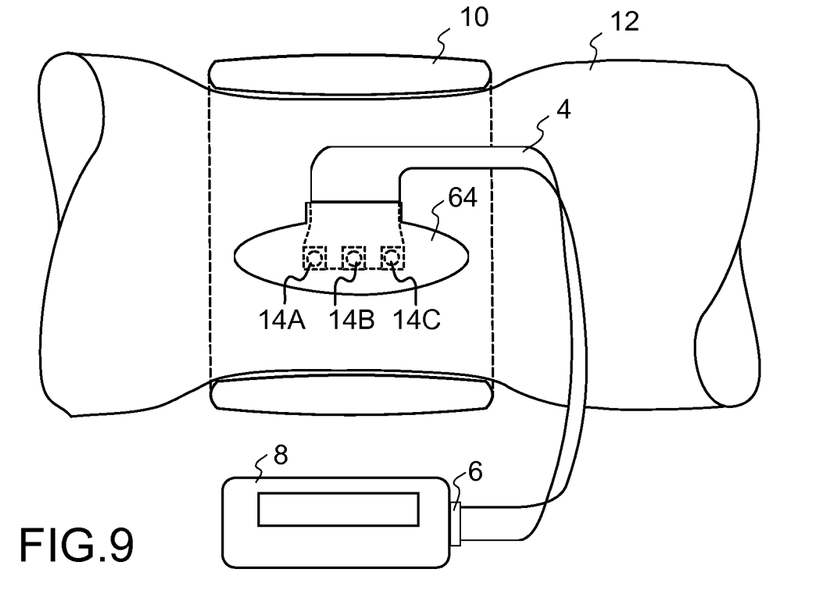
FIG. 9 is a schematic diagram depicting an alternative embodiment of this invention suitable for interface pressure and interface pressure gradient estimation.
Figure 10:
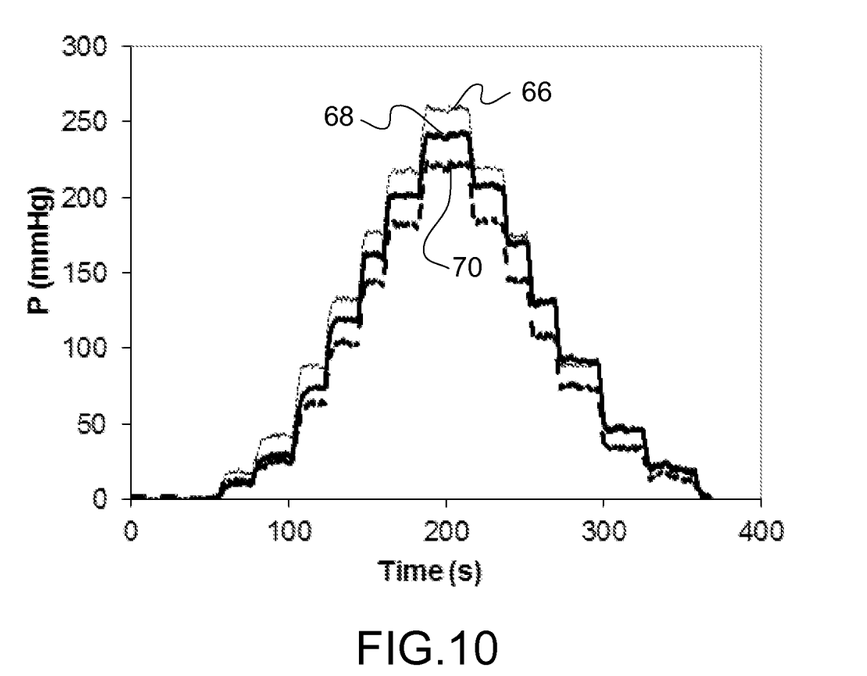
FIG. 10 illustrates the data flow from the biomedical interface pressure transducer of FIG. 9 showing the contemporaneous pressure at three different tourniquet-limb interface positions: proximal, central and distal.

Estimates of biomedical interface pressures at a plurality of interface locations may be obtained using the biomedical interface pressure transducer 64 illustrated in FIG. 9 which is constructed according to the principles of this invention. In the embodiment illustrated, three modified MEMS pressure sensors, 14A, 14B and 14C are integrated into the transducer forming an equally spaced linear array. The transducer provides estimates of the interface pressures arising centrally 68, and at relative proximal 66 and distal 70 sub-cuff locations as illustrated in FIG. 10. Clearly, this data may be used to estimate biomedical interface pressure gradients arising at tourniquet cuff-limb interfaces. It will be clear to those familiar in the art that the number and locations of the modified MEMS pressure sensors may be varied to suit specific applications. For instance, a biomedical interface pressure transducer, with a two dimensional array of integrated modified MEMS pressure sensors could be constructed following the principles of the current invention which would provide interface pressure profile or contour data from which tourniquet-limb contact area could be calculated in turn allowing estimation of the total force applied by the tourniquet to the limb or support tissue.

In applications where a lubrication gel is present at the tourniquet-tissue interface, the biomedical interface pressure transducer of this invention may be used without the shear relief membrane without adversely impacting the accuracy or reliability of the indicated interface pressure data.

The biomedical interface pressure transducer of this invention may be sterilized by heating in an autoclave or by exposure to sterilization gas.

It will be clear to those skilled in the art that alternative sensor signal chain designs may be used to convert the biomedical interface pressure transducer 2 measurement signal to a pressure value. For instance, the MEMS pressure sensor chip 40 may be selected from a range which includes integrated ADC, 64 BIT PROM memory, and digital interface integrated circuits. A microcontroller may be used to provide software adjustment of the digital signal available via standard three wire serial interface in order to provide dynamic temperature compensation for offset and span using factory pre calibrated coefficients stored in PROM memory. In addition the flexible interconnector assembly 4 may incorporate electrical screening to reduce RF noise interference in noisy environments. Furthermore, wireless transceivers may be integrated with the control means 8 to allow wireless communications between the biomedical interface pressure transducer apparatus and a remote computer or logging device.

While preferred embodiments of the invention have been described, changes in the construction and the arrangement of parts and the performance of steps can be made by those skilled in the art, which changes are encompassed within this invention as defined by the appended claims.

It will be appreciated that the transducer combines a modified MEMS pressure sensor, conformable semisolid body and flexible interconnector assembly in a single integrated solution which has a low profile, and is sufficiently flexible to allow conformation to body parts/tissue. Because of the extremely low profile of the sensor (minimally intrusive) and other structure elements it is relatively immune to "hammocking" errors and shear and frictionally induced measurement errors.

The invention claimed is:

1. A biomedical interface pressure transducer apparatus for estimating an interface pressure applied to living tissue by a medical tourniquet, medical device or other tissue comprising:

a MEMS pressure sensor mounted to a substrate and surrounded by a port that projects from the substrate to define an internal volume within the port, the port having an external surface that is opposite the substrate and that defines a sensing plane;

wherein the internal volume includes a first layer of gel adjacent to the sensor, and a second layer of gel material that is selected from a group consisting of RTV Silicone, polydimethyl siloxane (PDMS), Silicone Rubber, and Rubison premixed white silicone, and that is harder than the first layer and that fills the internal volume with the first layer being between the substrate and the second layer and such that a surface of the second layer is coplanar with the plane defined by the port surface;

a conformable semisolid body that surrounds the MEMS pressure sensor;

a membrane extending in the sensing plane and covering the port external surface, and covering the internal volume, the membrane being movable in the sensing plane;

wherein the MEMS pressure sensor produces a pressure signal indicative of the interface pressure applied to living tissue by the medical tourniquet, medical device or other tissue as transmitted by the membrane to the second and first layers;

a controller in communication with the MEMS pressure sensor for receiving the pressure signal, the controller providing power, signal conditioning, interfacing and display functions.

2. The apparatus of claim 1 wherein the MEMS pressure sensor is electrically connected to the controller using a patterned conductor on a flexible substrate.

3. The apparatus of claim 1 wherein the ratio of the area of a top surface of said second layer to a footprint area of the MEMS pressure sensor substrate is greater than 0.3.

4. The apparatus of claim 1 wherein the conformable body has a top planar face and a bottom planar face disposed substantially parallel to each other, said conformable semisolid body narrowing from the top planar face to the bottom planar face following a convex curved surface, said top planar face of said conformable semisolid body being substantially coplanar with a top surface of the second layer and said conformable semisolid body substantially enclosing said MEMS pressure sensor.

5. Apparatus as defined in claim 1 wherein the first layer has a lower viscosity than the second layer, and the second layer is substantially incompressible.

6. Apparatus as defined in claim 1 wherein the conformable semisolid body is formed from substantially incompressible material.

7. Apparatus as defined in claim 1 wherein the conformable semisolid body has physical dimensions and flexibility selected so that it conforms to tissue surfaces with radius of curvature greater than 10 mm and does not displace the pressure applying medical tourniquet or device more than 4 mm from said tissue surfaces.

8. Apparatus as defined in claim 1, wherein the membrane is a shear relief membrane with an inner surface and an outer surface, which substantially encloses the conformable semisolid body and the MEMS pressure sensor and which has freedom to move relative to said conformable semisolid body and said MEMS pressure sensor.

9. Apparatus as defined in claim 8 wherein the shear relief membrane is formed from a flexible material that has a low coefficient of friction and is substantially inextensible.

10. Apparatus as defined in claim 8 wherein a lubrication fluid or gel is distributed over a major proportion of the inner surface of the shear relief membrane.

11. The biomedical interface pressure transducer of claim 1, further comprising:
a sensor array comprising a plurality of MEMS pressure sensors as defined in claim 1;
wherein said sensor array produces a plurality of pressure signals indicative of the interface pressures applied to living tissue by the medical tourniquet, medical device or other tissue at a plurality of tissue locations; and wherein
the controller is in communication with the sensor array for receiving the pressure signals.

12. Apparatus as defined in claim 11 wherein the control means provides estimates of the pressure gradients at the interface between the medical tourniquet or device and the tissue.

13. A method of making a biomedical interface pressure transducer apparatus for estimating an interface pressure applied to living tissue by a medical tourniquet, medical device or other tissue comprising the steps of:
mounting to a substrate a MEMS pressure sensor that is surrounded by a port that projects from the substrate to define an internal volume within the port, wherein the port has an external surface that is opposite the substrate and that defines a sensing plane;
disposing in the internal volume a first layer of gel adjacent to the sensor and a second layer of gel material that is selected from a group consisting of RTV Silicone, polydimethyl siloxane (PDMS), Silicone Rubber, and Rubison premixed white silicone, and that is harder than the first layer and that fills the volume so that the first layer is between the substrate and the second layer and such that a surface of the second layer is coplanar with the sensing plane;
incorporating the MEMS pressure sensor into a conformable semisolid body that surrounds the MEMS pressure sensor with the second layer of material arranged to allow direct contact to continuum materials, wherein the MEMS pressure sensor produces a pressure signal indicative of the interface pressure applied to living tissue by the medical tourniquet, medical device or other tissue as transmitted by the continuum materials through the internal volume to the sensor;
providing a controller in communication with the MEMS pressure sensor for receiving the pressure signal, the controller providing power, signal conditioning, interfacing and display functions; and
enclosing the conformable semisolid body and the MEMS pressure sensor within a shear relief membrane that has an inner surface and an outer surface in a manner such that the membrane has freedom to move relative to said conformable semisolid body and said MEMS pressure sensor.

14. The method of claim 13 wherein the internal volume is partially filled with a bottom layer of MEMS protection material and a top layer of media isolation material, and further comprising the step of arranging the top surface of said media isolation material to be substantially coplanar with the external surface of said pressure sensor port.

15. The method of claim 13 further comprising the steps of:
configuring the conformable body to have a top planar face and a bottom planar face disposed substantially parallel to each other;
narrowing the conformable semisolid body from the top planar face to the bottom planar face following a convex curved surface;
forming the top planar face of the conformable semisolid body to be substantially coplanar with the top surface of the media isolation material of the MEMS pressure sensor; and
substantially enclosing the MEMS pressure sensor with the conformable semisolid body.

16. The method of claim 13, including the step of forming the membrane of flexible material that has a low coefficient of friction and is substantially inextensible.

\* \* \* \* \*